United States Patent
Ogawa et al.

(10) Patent No.: US 10,015,964 B2
(45) Date of Patent: Jul. 10, 2018

(54) FUNGICIDAL COMPOSITION AND METHOD FOR CONTROLLING PLANT DISEASES

(75) Inventors: Munekazu Ogawa, Kusatsu (JP); Yuzuka Kawai, Kusatsu (JP)

(73) Assignee: Ishihara Sangyo Kaisha, Ltd., Osaka-shi (JP)

(*) Notice: Subject to any disclaimer, the term of this patent is extended or adjusted under 35 U.S.C. 154(b) by 44 days.

(21) Appl. No.: 14/130,621

(22) PCT Filed: Jun. 15, 2012

(86) PCT No.: PCT/JP2012/065925
§ 371 (c)(1),
(2), (4) Date: Jan. 2, 2014

(87) PCT Pub. No.: WO2013/008604
PCT Pub. Date: Jan. 17, 2013

(65) Prior Publication Data
US 2014/0128411 A1  May 8, 2014

(30) Foreign Application Priority Data
Jul. 8, 2011 (JP) .................. 2011-151807

(51) Int. Cl.
*A01N 43/40* (2006.01)
*A01N 43/56* (2006.01)
*A01N 43/90* (2006.01)

(52) U.S. Cl.
CPC ............. *A01N 43/40* (2013.01); *A01N 43/56* (2013.01); *A01N 43/90* (2013.01)

(58) Field of Classification Search
None
See application file for complete search history.

(56) References Cited

U.S. PATENT DOCUMENTS

| | | |
|---|---|---|
| 6,770,662 B2 | 8/2004 | Nishide et al. |
| 2006/0089390 A1 | 4/2006 | Nishide et al. |
| 2006/0194849 A1 | 8/2006 | Nishide et al. |
| 2009/0221588 A1 | 9/2009 | Haas et al. |
| 2009/0247763 A1 | 10/2009 | Nishide et al. |
| 2011/0053966 A1* | 3/2011 | Klittich et al. ............ 514/274 |
| 2011/0104307 A1 | 5/2011 | Ogawa et al. |
| 2011/0280959 A1 | 11/2011 | Nishide et al. |
| 2012/0135088 A1 | 5/2012 | Nishide et al. |

FOREIGN PATENT DOCUMENTS

| | | |
|---|---|---|
| EP | 1 679 003 A1 | 7/2006 |
| JP | 2009-532403 A | 9/2009 |
| SU | 722459 A3 | 3/1980 |
| WO | WO 02/02527 A1 | 1/2002 |
| WO | WO 2005/041663 A1 | 5/2005 |
| WO | WO 2007/115766 A1 | 10/2007 |
| WO | WO2009090181 A2 * | 7/2009 |
| WO | WO 2010/002026 A2 | 1/2010 |
| WO | WO 2010/002026 A3 | 1/2010 |
| WO | WO 2011/117271 A2 | 9/2011 |
| WO | WO 2012/016989 A2 | 2/2012 |
| WO | WO 2012/031061 A2 | 3/2012 |

OTHER PUBLICATIONS

Pyriofenone [online], [Retrieved on: Aug. 31, 2015]. Retrieved from the Internet: <URL:http://www.alanwood.net/pesticides/pyriofenone.html>.*
U.S. Appl. No. 14/136,614, filed Dec. 20, 2013, Nishide, et al.
U.S. Appl. No. 14/572,237, filed Dec. 16, 2014, Ogawa, et al.
International Search Report issued Aug. 20, 2012 in Application No. PCT/JP2012/065925.
"FRAC Code List ©*: Fungicides sorted by mode of action (including FRAC Code numbering)", Retrieved from the Internet: URL http://www.frac.info/frac/publication/anhang/FRAC_Code_List_2010.pdf, XP55035028, Dec. 31, 2009, pp. 1-10.
Office Action issued Aug. 28, 2015 in Russian Patent Application No. 2014104501.
Japanese Office Action issued Jan. 5, 2016 in corresponding Japanese Patent Application No. JP 2012-131806 with English translation, 8 pp.

* cited by examiner

*Primary Examiner* — Kendra D Carter
*Assistant Examiner* — Taina D Matos Negron
(74) *Attorney, Agent, or Firm* — Oblon, McClelland, Maier & Neustadt, L.L.P.

(57) ABSTRACT

The present invention provides a fungicidal composition useful as an agricultural and horticultural fungicide having remarkably improved controlling effects against plant diseases, and a method for controlling plant diseases using the composition. A fungicidal composition comprising, as active ingredients, (a) 3-(2,3,4-trimethoxy-6-methylbenzoyl)-5-chloro-2-methoxy-4-methylpyridine (pyriofenone) or its salt and (b) at least one fungicide selected from the group consisting of bixafen, fluxapyroxad, penflufen, isopyrazam, fluopyram, ametoctradin, fenpyrazamine and sedaxane, and a method for controlling plant diseases, which comprises applying the fungicidal composition to plants.

15 Claims, No Drawings

FUNGICIDAL COMPOSITION AND METHOD FOR CONTROLLING PLANT DISEASES

TECHNICAL FIELD

The present invention relates to a fungicidal composition useful as an agricultural and horticultural fungicide having remarkably improved controlling effects against plant diseases, and a method for controlling plant diseases by using such a composition.

BACKGROUND ART

Patent Document 1 discloses that a benzoylpyridine derivative which is an active ingredient of the fungicidal composition in the present invention is useful as a fungicide and may be mixed with or used in combination with another fungicide as the case requires. Further, Patent Documents 2 and 3 disclose that by use of the benzoylpyridine derivative in combination with another specific fungicide, it is possible to obtain a fungicidal composition having excellent synergistic effects. Further, Patent Document 4 discloses a composition comprising the benzoylpyridine derivative and isopyrazam, and Patent Document 5 also discloses a composition comprising the benzoylpyridine derivative and fluxapyroxad, bixafen, fluopyram, isopyrazam, sedaxane, penflufen, etc.

However, it has not specifically been known that the fungicidal composition in the present invention has remarkably excellent fungicidal effects.

PRIOR ART DOCUMENTS

Patent Documents

Patent Document 1: WO02/02527
Patent Document 2: WO2005/041663
Patent Document 3: WO2010/002026
Patent Document 4: WO2007/115766
Patent Document 5: WO2012/016989

DISCLOSURE OF INVENTION

Technical Problem

Each of active ingredients of the fungicidal composition in the present invention, may be inadequate in its controlling effect against a specific plant disease, or its residual effect may last only a relatively short time, and thus, depending upon the condition for application, it may practically have only an inadequate controlling effect against plant diseases.

Solution to Problem

The present inventors have conducted a research to solve the above problems and as a result, found that when (a) 3-(2,3,4-trimethoxy-6-methylbenzoyl)-5-chloro-2-methoxy-4-methylpyridine or its salt and (b) at least one fungicide selected from the group consisting of bixafen, fluxapyroxad, penflufen, isopyrazam, fluopyram, ametoctradin, fenpyrazamine and sedaxane are used in combination, an unexpectedly excellent fungicidal effect can be obtained as compared with a case where the respective compounds are used alone, and accomplished the present invention.

That is, the present invention provides a fungicidal composition comprising, as active ingredients, (a) 3-(2,3,4-trimethoxy-6-methylbenzoyl)-5-chloro-2-methoxy-4-methylpyridine or its salt (hereinafter sometimes referred to simply as a component (a)) and (b) at least one fungicide selected from the group consisting of bixafen, fluxapyroxad, penflufen, isopyrazam, fluopyram, ametoctradin, fenpyrazamine and sedaxane (hereinafter sometimes referred to simply as a component (b)). Further, the present invention provides a method for controlling plant diseases, which comprises applying the above fungicidal composition to plants.

Advantageous Effects of Invention

The fungicidal composition of the present invention presents a synergistic effect i.e. a fungicidal effect higher than the mere addition of the respective fungicidal effects of the active ingredients, against plant diseases. More specifically, even if components (a) and (b) being active ingredients of the fungicidal composition of the present invention show only an inadequate controlling effect against specific plant diseases when they are used alone, respectively, by using them in combination, they show a synergistic controlling effect against plant diseases and thus exhibit a practically sufficient controlling effect.

DESCRIPTION OF EMBODIMENTS 3-(2,3,4-Trimethoxy-6-methylbenzoyl)-5-chloro-2-methoxy-4-methylpyridine as the component (a) in the present invention can be obtained by a production process as disclosed in the above Patent Documents 1 and 2. Further, this is a compound known by a common name pyriofenone.

The component (a) may be a salt. The salt may be any agriculturally acceptable salt, and may, for example, be an inorganic acid salt such as a hydrochloride, a perchlorate, a sulfate or a nitrate; or an organic acid salt such as an acetate, a fumarate or a methanesulfonate.

Each of bixafen, fluxapyroxad, penflufen, isopyrazam, fluopyram, ametoctradin, fenpyrazamine and sedaxane as the component (b) in the present invention is a compound disclosed as a fungicide in The Pesticide Manual (15th edition, BRITISH CROP PROTECTION COUNCIL) or SHIBUYA INDEX 15th edition (SHIBUYA INDEX RESEARCH GROUP).

Among them, bixafen, fluxapyroxad, penflufen, isopyrazam, sedaxane and fluopyram are electron transporting composite II inhibitors having a carboxamide structure. More specifically, bixafen, fluxapyroxad, penflufen, isopyrazam and sedaxane are electron transporting composite II inhibitors classified into pyrazole carboxamide compounds, and fluopyram is an electron transporting composite II inhibitor classified into pyridinyl-ethylbenzamide compounds.

Among components (b) in the present invention, bixafen, fluxapyroxad, penflufen, fluopyram, ametoctradin and fenpyrazamine, which exhibit higher synergistic effects when used in combination with the component (a), are preferred, and bixafen and fluopyram are more preferred.

The fungicidal composition of the present invention is useful particularly as an agricultural and horticultural fungicide. As the agricultural and horticultural fungicide, it is effective for controlling diseases such as powdery mildew, scab, rust, snow mold, snow blight, loose smut, eye spot, leaf spot or glume blotch of cereals (*Hordeum vulgare, Tricum aestivum*, etc.); melanose or scab of citrus (*Citrus* spp., etc.); blossom blight, powdery mildew, *Alternaria* leaf spot, scab, anthracnose, blotch, ring rot, fly speck, sooty blotch or fruit spot of apple (*Malus pumila*); scab, black spot, powdery mildew or *Phytophthora* rot of pear (*Pyrus Pyrifolia*, var. culta); ring rot or powdery mildew of European pear (*Pyrus communis*); brown rot, scab or *Phomopsis* rot of peach (*Prunus persica*, etc.); anthracnose, ripe rot, powdery mildew, downy mildew, gray mold, *Isariopsis* leaf spot or swelling arm of grape (*Vitis vinifera* spp., etc.); anthracnose, leaf spot, powdery mildew or fly speck of Japanese persimmon (*Diospuros kaki*, etc.); anthracnose, powdery mildew, gummy stem blight, downy mildew, *Phytophthora* rot or *Cercospora* leaf spot of cucurbit (*Cucumis melo*, etc.); early blight, leaf mold, late blight, gray mold or powdery mildew of tomato (*Lycopersicon esculentum*); *Alternaria* leaf spot of cruciferous vegetables (*Brassica* sp., *Raphanus* sp., etc); early blight or late blight of potato (*Solanum tuberosum*); powdery mildew, gray mold or anthracnose of strawberry (*Fraparia*, etc.); and gray mold or powdery mildew of various crops. It is particularly effective against plant diseases of cereals, fruits (particularly apple, pear and European pear) and vegetables (particularly cucurbit and tomato). Further, it is effective also for controlling soil diseases caused by plant pathogens such as *Fusarium, Pythium, Rhizoctonia, Verticillium* and *Plasmodiophora*.

The components (a) and (b) constituting the fungicidal composition of the present invention are, in the same manner as conventional agricultural chemicals, mixed with various adjuvants and formulated into various formulations such as a dust, granules, water dispersible granules, a wettable powder, a water-based suspension concentrate, an oil-based suspension concentrate, water soluble granules, an emulsifiable concentrate, a soluble concentrate, a paste, an aerosol and an ultra low-volume formulation. However, so long as the purpose of the present invention can be accomplished, any type of formulation which is commonly used in this field is applicable. Such adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethyl sulfoxide, dimethylformamide, dimethylacetamide, N-methyl-2-pyrrolidone and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected from those known in this field so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed. The blend ratio of the components (a) and (b) to the various adjuvants is usually from 0.005:99.995 to 95:5, preferably from 0.2:99.8 to 90:10. In the actual application of such a formulation, it may be used as it is, or may be diluted to a predetermined concentration with a diluent such as water, and various spreaders may be added thereto, as the case requires.

Further, the fungicidal composition of the present invention may be mixed with or used in combination with other agricultural chemicals such as a fungicide, an insecticide, a miticide, a nematicide, a soil pesticide, an antivirus agent, an attractant, a herbicide and a plant growth regulating agent, whereby more excellent effects may sometimes be obtained.

The active ingredient compounds of a fungicide in the above-mentioned other agricultural chemicals, include, for example, (by common names, some of them are still in an application stage, or test codes of Japan Plant Protection Association):

anilinopyrimidine compounds such as mepanipyrim, pyrimethanil and cyprodinil;

triazolopyrimidine compounds such as 5-chloro-7-(4-methylpiperidin-1-yl)-6-(2,4,6-trifluorophenyl)[1,2,4]triazolo[1,5-a]pyrimidine;

pyridinamine compounds such as fluazinam;

azole compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, prothioconazole, triadimenol, flutriafol, difenoconazole, fluquinconazole, fenbuconazole, bromuconazole, diniconazole, tricyclazole, probenazole, simeconazole, pefurazoate, ipconazole, imibenconazole, azaconazole, triticonazole and imazalil;

quinoxaline compounds such as quinomethionate;

dithiocarbamate compounds such as maneb, zineb, mancozeb, polycarbamate, metiram, propineb and thiram;

organic chlorine compounds such as fthalide, chlorothalonil and quintozene;

imidazole compounds such as benomyl, thiophanate-methyl, carbendazim, thiabendazole, fuberiazole and cyazofamid;

cyanoacetamide compounds such as cymoxanil;

anilide compounds such as matalaxyl, metalaxyl-M (another name: mefenoxam), oxadixyl, ofurace, benalaxyl, benalaxyl-M (another name: kiralaxyl, chiralaxyl), furalaxyl, cyprofuram, carboxin, oxycarboxin, thifluzamide, boscalid, isotianil and tiadinil;

sulfamide compounds such as dichlofluanid;

copper compounds such as cupric hydroxide and oxine copper;

isoxazole compounds such as hymexazol;

organophosphorus compounds such as fosetyl-Al, tolclofos-methyl, S-benzyl O,O-diisopropylphosphorothioate, O-ethyl S,S-diphenylphosphorodithioate, aluminum ethyl-hydrogen phosphonate, edifenphos and iprobenfos;

phthalimide compounds such as captan, captafol and folpet;

dicarboxyimide compounds such as procymidone, iprodione and vinclozolin;

benzanilide compounds such as flutolanil, mepronil and benodanil;

amide compounds such as penthiopyrad, furametpyr, silthiopham, fenoxanil and fenfuram;

benzamide compounds such as zoxamide;

piperazine compounds such as triforine;

pyridine compounds such as pyrifenox;

carbinol compounds such as fenarimol and nuarimol;

piperidine compounds such as fenpropidin;

morpholine compounds such as fenpropimorph and tridemorph;

organotin compounds such as fentin hydroxide and fentin acetate;

urea compounds such as pencycuron;

cinnamic acid compounds such as dimethomorph and flumorph;

phenyl carbamate compounds such as diethofencarb;

cyanopyrrole compounds such as fludioxonil and fenpiclonil;

strobilurin compounds such as azoxystrobin, kresoxim-methyl, metominostrobin, trifloxystrobin, picoxystrobin, oryzastrobin, dimoxystrobin, pyraclostrobin, fluoxastrobin, enestroburin, pyraoxystrobin and pyrametostrobin;

oxazolidinone compounds such as famoxadone;

thiazolecarboxamide compounds such as ethaboxam;

valinamide compounds such as iprovalicarb and benthiavalicarb-isopropyl;

acylamino acid compounds such as methyl N-(isopropoxycarbonyl)-L-valyl-(3RS)-3-(4-chlorophenyl)-β-alaninate (valiphenalate);

imidazolinone compounds such as fenamidone;

hydroxyanilide compounds such as fenhexamid;

benzenesulfonamide compounds such as flusulfamide;

oxime ether compounds such as cyflufenamid;

anthraquinone compounds;

crotonic acid compounds;

antibiotics such as validamycin, kasugamycin and polyoxins;

guanidine compounds such as iminoctadine and dodine;

quinoline compounds such as tebufloquin;

thiazolidine compounds such as flutianil;

sulfur compounds such as sulfur;

and other compounds such as pyribencarb, isoprothiolane, pyroquilon, diclomezine, quinoxyfen, propamocarb hydrochloride, chloropicrin, dazomet, metam-sodium, metrafenone, UBF-307, diclocymet, proquinazid, amisulbrom (another name: amibromdole), mandipropamid, fluopicolide, carpropamid, meptyldinocap, N-[(3',4'-dichloro-1,1-dimethyl)phenacyl]-3-trifluoromethyl-2-pyridinecarboxamide, N-[(3',4'-dichloro-1,1-dimethyl)phenacyl]-3-methyl-2-thiophenecarboxamide, N-[(3',4'-dichloro-1,1-dimethyl)phenacyl]-1-methyl-3-trifluoromethyl-4-pyrazolecarboxamide, N-[[2'-methyl-4'-(2-propyloxy)-1,1-dimethyl]phenacyl]-3-trifluoromethyl-2-pyridinecarboxamide, N-[[2'-methyl-4'-(2-propyloxy)-1,1-dimethyl]phenacyl]-3-methyl-2-thiophenecarboxamide, N-[[2'-methyl-4'-(2-propyloxy)-1,1-dimethyl]phenacyl]-1-methyl-3-trifluoromethyl-4-pyrazolecarboxamide, N-[[4'-(2-propyloxy)-1,1-dimethyl]phenacyl]-3-trifluoromethyl-2-pyridinecarboxamide, N-[[4'-(2-propyloxy)-1,1-dimethyl]phenacyl]-3-methyl-2-thiophenecarboxamide, N-[[4'-(2-propyloxy)-1,1-dimethyl]phenacyl]-1-methyl-3-trifluoromethyl-4-pyrazolecarboxamide, N-[[2'-methyl-4'-(2-pentyloxy)-1,1-dimethyl]phenacyl]-3-trifluoromethyl-2-pyridinecarboxamide, N-[[4'-(2-pentyloxy)-1,1-dimethyl]phenacyl]-3-trifluoromethyl-2-pyridinecarboxamide, ferimzone, spiroxamine, S-2200, ZF-9646, BCM-061, BCM-062, S-8606, DKF-1001, MF-1001, MF-1002, NC-223, NK-1001, SB-4303 and BAF-1107.

The active ingredient compounds of insect pest control agents, such as the insecticide, the miticide, the nematicide and the soil insect pesticide in the above-mentioned other agricultural chemicals, include, for example, (by common names, some of them are still in an application stage, or test codes of Japan Plant Protection Association):

organic phosphate compounds, such as profenofos, dichlorvos, fenamiphos, fenitrothion, EPN, diazinon, chlorpyrifos, chlorpyrifos-methyl, acephate, prothiofos, fosthiazate, cadusafos, disulfoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet and phorate;

carbamate compounds, such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC and fenothiocarb;

nereistoxin derivatives, such as cartap, thiocyclam, bensultap and thiosultap-sodium;

organic chlorine compounds, such as dicofol, tetradifon, endosulfan, dienochlor and dieldrin;

organic metal compounds, such as fenbutatin oxide and cyhexatin;

pyrethroid compounds, such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin and flumethrin;

benzoylurea compounds, such as diflubenzuron, chlorfluazuron, teflubenzuron, flufenoxuron, triflumuron, hexaflumuron, lufenuron, novaluron, noviflumuron, bistrifluron and fluazuron;

juvenile hormone-like compounds, such as methoprene, pyriproxyfen, fenoxycarb and diofenolan;

pyridazinone compounds, such as pyridaben;

pyrazole compounds, such as fenpyroximate, fipronil, tebufenpyrad, ethiprole, tolfenpyrad, acetoprole, pyrafluprole and pyriprole;

neonicotinoids, such as imidacloprid, nitenpyram, acetamiprid, thiacloprid, thiamethoxam, clothianidin, nidinotefuran, dinotefuran and nithiazine;

hydrazine compounds, such as tebufenozide, methoxyfenozide, chromafenozide and halofenozide;

pyridine compounds, such as flonicamid;

tetronic acid compounds, such as spirodiclofen;

strobilurin compounds, such as fluacrypyrim;

pyrimidinamine compounds, such as flufenerim;

dinitro compounds;

organic sulfur compounds;

urea compounds;

triazine compounds;

hydrazone compounds;

other compounds, such as buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, spiromesifen, spirotetramat, propargite, clofentezine, metaflumizone, flubendiamide, cyflumetofen, chlorantraniliprole, cyenopyrafen, pyrifluquinazone, fenazaquin, amidoflumet, chlorobenzoate, sulfluramid, hydramethylnon, metaldehyde, HGW-86, AKD-1022, ryanodine, pyridalyl and verbutin. Further, it may be mixed with or used in combination with microbial agricultural chemicals, such as *Bacillus thuringiensis* aizawai, *Bacillus thuringiensis* kurstaki, *Bacillus thuringiensis* israelensis, *Bacillus thuringiensis* japonensis, *Bacillus thuringiensis* tenebrionis or insecticidal crystal proteins produced by *Bacillus thuringiensis*, insect viruses, etomopathogenic fungi, and nematophagous fungi: antibiotics or semisynthetic antibiotics, such as avermectin, emamectin benzoate, milbemectin, milbemycin, spinosad, ivermectin, lepimectin, DE-175, abamectin, emamectin and spinetoram; natural products, such as azadirachtin, and rotenone; and repellents, such as deet.

In the fungicidal composition of the present invention, the suitable mixing weight ratio of the component (a) to the component (b) is preferably from 1:5,000 to 5,000:1, more preferably from 1:1,000 to 1,000:1, particularly preferably from 1:500 to 500:1.

A method for controlling plant diseases, which comprises applying the fungicidal composition of the present invention to agricultural and horticultural plants, is also included in the present invention. The concentration of the fungicidal composition of the present invention cannot generally be defined, as it varies depending upon the crop plants to be treated, the application method, the type of the formulation, the dose, etc. However, it is adjusted so that the concentration of the component (a) is preferably from 200 to 0.05 ppm, more preferably from 100 to 0.1 ppm, and the concentration of the component (b) is preferably from 1,000 to 1 ppm, more preferably from 1,000 to 10 ppm, particularly preferably from 500 to 20 ppm, in the case of foliar treatment. In the case of soil treatment, the concentration is adjusted so that the concentration of the component (a) is preferably from 200 to 10 g/ha, more preferably from 100 to 20 g/ha and the concentration of the component (b) is preferably from 1,000 to 50 g/ha, more preferably from 500 to 40 g/ha.

The formulation containing the fungicidal composition of the present invention or a diluted product thereof may be applied by an application method which is commonly used, such as spraying (such as spraying, jetting, misting, atomizing, powder or grain scattering, or dispersing in water), soil application (such as mixing or drenching) or surface application (such as coating, powdering or covering). Further, it may be applied also by a so-called ultra low-volume application method. In this method, the formulation may be composed of 100% of the active ingredients.

EXAMPLES

Now, Test Examples of the present invention will be described, but it should be understood that the present invention is by no means restricted thereto.

Test Example 1

Test on Preventive Effect Against Wheat Powdery Mildew

Wheat (cultivar: Norin-61) was cultivated in a plastic pot having a diameter of 7.5 cm, and when it reached 1.5-leaf stage, a chemical solution having each test compound adjusted to a prescribed concentration, was applied by a spray gun in an amount of 5 ml/seedling. After the chemical solution dried, conidia of *Erysiphe graminis* were dusted and inoculated and maintained in a constant temperature chamber at 20° C. From 6 to 8 days after the inoculation, the area of sporulation was investigated, and the control value was determined in accordance with the following formula, and the results are shown in Tables 1 to 7. The area of sporulation in the non-treated plot was determined in the same manner as for the treated plot except that water was applied by a spray gun instead of the chemical solution.

Control value=$(1-a/b) \times 100$ a: area of sporulation in the treated plot b: area of sporulation in the non-treated plot Based on the obtained control value, an expected value (control value) was calculated by the Colby's formula. The expected values by the Colby's formula are also shown in brackets ( ) in Tables 1 to 7.

When the experimental value is higher than the expected value, the fungicidal composition of the present invention has a synergistic effect against wheat powdery mildew.

TABLE 1

| Concentration of | Concentration of component (a) | | | |
|---|---|---|---|---|
| bixafen | 0.5 ppm | 0.25 ppm | 0.125 ppm | 0 ppm |
| 500 ppm | 97.5(75) | 95(65) | 95(65) | 50 |
| 250 ppm | 97.5(50) | 90(30) | 50(30) | 0 |
| 0 ppm | 50 | 30 | 30 | |

TABLE 2

| Concentration of | Concentration of component (a) | | | |
|---|---|---|---|---|
| isopyrazam | 0.5 ppm | 0.25 ppm | 0.125 ppm | 0 ppm |
| 31 ppm | 100(95) | 97.5(93) | 97.5(93) | 90 |
| 16 ppm | 97.5(75) | 95(65) | 92.5(65) | 50 |
| 0 ppm | 50 | 30 | 30 | |

TABLE 3

| Concentration of | Concentration of component (a) | | | |
|---|---|---|---|---|
| fluopyram | 0.5 ppm | 0.25 ppm | 0.125 ppm | 0 ppm |
| 31 ppm | 100(85) | 100(79) | 97.5(79) | 70 |
| 16 ppm | 100(70) | 92.5(58) | 72.5(58) | 40 |
| 0 ppm | 50 | 30 | 30 | |

TABLE 4

| Concentration of | Concentration of component (a) | | | |
|---|---|---|---|---|
| ametoctradin | 0.5 ppm | 0.25 ppm | 0.125 ppm | 0 ppm |
| 400 ppm | 100(57.5) | 100(40.5) | 95(40.5) | 15 |
| 200 ppm | 100(50) | 95(30) | 90(30) | 0 |
| 0 ppm | 50 | 30 | 30 | |

TABLE 5

| Concentration of sedaxane | Concentration of component (a) | | |
|---|---|---|---|
| | 0.5 ppm | 0.125 ppm | 0 ppm |
| 12.5 ppm | 92.5(58) | 60(30) | 30 |
| 6.3 ppm | 92.5(40) | 60(0) | 0 |
| 0 ppm | 40 | 0 | |

TABLE 6

| Concentration of fenpyrazamine | Concentration of component (a) | | |
|---|---|---|---|
| | 0.5 ppm | 0.125 ppm | 0 ppm |
| 250 ppm | 70(40) | 30(0) | 0 |
| 63 ppm | 70(40) | 30(0) | 0 |
| 0 ppm | 40 | 0 | |

TABLE 7

| Concentration of fluxapyroxad | Concentration of component (a) | | |
|---|---|---|---|
| | 0.5 ppm | 0.125 ppm | 0 ppm |
| 50 ppm | 95(70) | 82.5(50) | 50 |
| 6.3 ppm | 90(58) | 70(30) | 30 |
| 0 ppm | 40 | 0 | |

Test Example 2

Test on Preventive Effect Against Kidney Bean Gray Mold

Kidney bean (cultivar: Taishokintoki) was cultivated in a plastic pot having a diameter of 12 cm, and when it reached 3 to 4-leaf stage, a chemical solution having each test compound adjusted to a prescribed concentration, was applied by a spray gun in an amount of 10 ml/seedling. After the chemical solution dried, a suspension of conidia of *Botrytis cinerea* was blotted on a paper disk having a diameter of 8 mm for implantation inoculation and maintained in a constant temperature chamber at 20° C. Upon expiration of 3 days from the inoculation, the lesion area was investigated, and the control value was determined in accordance with the following formula, and the results are shown in Table 8. The lesion area in the non-treated plot was determined in the same manner as for the treated plot except that water was applied by a spray gun instead of the chemical solution.

Control value=$(1-a/b) \times 100$ a: lesion area in the treated plot
b: lesion area in the non-treated plot Based on the obtained control value, an expected value (control value) was calculated by the Colby's formula. The expected values by the Colby's formula are also shown in brackets ( ) in Table 8.

When the experimental value is higher than the expected value, the fungicidal composition of the present invention has a synergistic effect against kidney bean gray mold.

TABLE 8

| Concentration of penflufen | Concentration of component (a) | | |
|---|---|---|---|
| | 400 ppm | 200 ppm | 0 ppm |
| 100 ppm | 95(50) | 92.5(50) | 50 |
| 50 ppm | 70(40) | 70(40) | 40 |
| 0 ppm | 0 | 0 | |

Now, Formulation Examples of the present invention will be described below. However, the blend ratio, the type of formulation or the like in the present invention is by no means restricted to the following Examples.

Formulation Example 1

| (a) Kaolin | 78 parts by weight |
|---|---|
| (b) Condensate of β-naphthalenesulfonic acid sodium salt with formalin | 2 parts by weight |
| (c) Polyoxyethylene alkylaryl sulfate | 5 parts by weight |
| (d) Hydrated amorphous silicon dioxide | 15 parts by weight |

A mixture of the above components, the component (a) and the component (b) are mixed in a weight ratio of 8:1:1 to obtain a wettable powder.

Formulation Example 2

| (a) Component (a) | 0.5 part by weight |
|---|---|
| (b) Component (b) | 0.5 part by weight |
| (c) Bentonite | 20 parts by weight |
| (d) Kaolin | 74 parts by weight |
| (e) Sodium lignin sulfonate | 5 parts by weight |

An appropriate amount of water for granulation is added to the above components and mixed, and the mixture is granulated to obtain granules.

Formulation Example 3

| (a) Component (a) | 2 parts by weight |
|---|---|
| (b) Component (b) | 3 parts by weight |
| (c) Talc | 95 parts by weight |

The above components are uniformly mixed to obtain a dust.

The entire disclosure of Japanese Patent Application No. 2011-151807 filed on Jul. 8, 2011 including specification, claims, drawings and abstract is incorporated herein by reference in its entirety.

The invention claimed is:

1. A fungicidal composition consisting of (a) 3-(2,3,4-trimethoxy-6-methylbenzoyl)-5-chloro-2-methoxy-4-methylpyridine or a salt thereof, (b) at least one fungicide selected from the group consisting of bixafen, fluxapyroxad, penflufen, isopyrazam, fluopyram, ametoctradin, fenpyrazamine and sedaxane and (c) at least one adjuvant, wherein the mixing weight ratio of (a) to (b) is from 1:500 to 500:1.

2. The fungicidal composition according to claim 1, wherein (b) s at least one fungicide selected from the group consisting of bixafen, fluxapyroxad, penflufen, isopyrazam, fluopyram, ametoctradin and fenpyrazamine.

3. The fungicidal composition according to claim 1, wherein (b) is at least one fungicide selected from the group consisting of bixafen, fluxapyroxad, penflufen, fluopyram, ametoctradin and fenpyrazamine.

4. A method for controlling plant diseases, which comprises applying a fungicidal composition consisting of (a) 3-(2,3,4-trimethoxy-6-methylbenzoyl)-5-chloro-2-methoxy-4-methylpyridine or a salt thereof, (b) at least one fungicide selected from the group consisting of bixafen, fluxapyroxad, penflufen, isopyrazam, fluopyram, ametoctradin, fenpyrazamine and sedaxane, and (c) at least one adjuvant to plants, wherein component (a) and component (b) are contained in said fungicidal composition at mixing weight ratio ranging from 1:500 to 500:1.

5. The method for controlling plant diseases according to claim 4, wherein (b) is at least one fungicide selected from the group consisting of bixafen, fluxapyroxad, penflufen, isopyrazam, fluopyram, ametoctradin and fenpyrazamine.

6. The fungicidal composition according to claim 1, wherein component (a) and component (b) are contained at a blend ratio ranging from 0.005:99.995 to 95:5.

7. The fungicidal composition according to claim 1, wherein component (a) and component (b) are contained at a blend ratio ranging from 0.2:99.8 to 90:10.

8. The method for controlling plant diseases according to claim 4, wherein said applying is a foliar application.

9. The method for controlling plant diseases according to claim 8, wherein component (a) is applied at a concentration ranging from 200 to 0.05 ppm.

10. The method for controlling plant diseases according to claim 8, wherein component (b) is applied at a concentration ranging from 1,000 to 1 ppm.

11. The method for controlling plant diseases according to claim 8, wherein component (a) is applied at a concentration ranging from 200 to 0.05 ppm and component (b) is applied at a concentration ranging from 1,000 to 1 ppm.

12. The method for controlling plant diseases according to claim 4, wherein said applying is a soil application.

13. The method for controlling plant diseases according to claim 12, wherein component (a) is applied at a concentration ranging from 200 to 10 g/ha.

14. The method for controlling plant diseases according to claim 12, wherein component (h) is applied at a concentration ranging from 1,000 to 50 g/ha.

15. The method for controlling plant diseases according to claim 12, wherein component (a) is applied at a concentration ranging from 200 to 10 g/ha and component (b) is applied at a concentration ranging from 1,000 to 50 g/ha.

* * * * *